United States Patent [19]

Szejtli et al.

[11] Patent Number: 4,774,232
[45] Date of Patent: Sep. 27, 1988

[54] BILE-SUBSTITUTING METHOD OF TREATMENT FOR THE PROMOTION OF FAT DIGESTION

[75] Inventors: József Szejtli; Lajos Szente; Katalin Kálóy; Jenö Marton; Andrea Gerlóczy, all of Budapest, Hungary

[73] Assignee: Chinoin Gyogyszer Es Vegyeszeti Termak Ek Gyara Rt, Budapest, Hungary

[21] Appl. No.: 946,684

[22] Filed: Dec. 24, 1986

Related U.S. Application Data

[63] Continuation-in-part of Ser. No. 817,428, Jan. 9, 1986, abandoned.

[30] Foreign Application Priority Data

Jan. 10, 1985 [HU] Hungary ............... 2251-75/85

[51] Int. Cl.$^4$ ............................................. A61K 31/70
[52] U.S. Cl. ..................................................... 514/58
[58] Field of Search ......................................... 514/58

[56] References Cited

FOREIGN PATENT DOCUMENTS 0046228 3/1984 Japan ..................................... 514/38

OTHER PUBLICATIONS

Imao et al., *Chemical Abstracts* vol. 103, 1983 No. 42475j.
Szabo et al., *Chemical Abstracts*, vol. 96, p. 10, 1982, No. 14948j.
Szabo et al., *Chemical Abstracts*, vol. 98, p. 10, 1983, No. 11054v.

*Primary Examiner*—J. R. Brown
*Assistant Examiner*—Elli Peselev
*Attorney, Agent, or Firm*—Herbert Dubno; Jonathan Myers

[57] ABSTRACT

The invention relates to a method of promoting the fat digestion and absorption, which comprises orally administering to an animal subject a partially methylated-β-cyclodextrin optionally together with pharmaceutically acceptable auxiliary and/or additive materials.

3 Claims, No Drawings

BILE-SUBSTITUTING METHOD OF TREATMENT FOR THE PROMOTION OF FAT DIGESTION

This is a continuation-in-part of co-pending application Ser. No. 817,428, filed on 1/9/86, now abandoned.

The invention relates to a method of treatment as a substitute for bile to promote the fat digestion and absorption, which comprises orally administering a methylated β-cyclodextrin for replacing the natural bile.

The bile is a discharge excreted by the liver cells which either flows into the duodenum or is transitorily stored and partially concentrated in the gall bladder and similarly passed to the duodenum according to the needs of the digestion.

The so-called liver bile, which is immediately discharged, is always thin whereas the bladder bile which is discharged from the bladder, is significantly thicker and is frequently 10-fold concentrated.

Lipids, for the most part triglycerides, but which also includes mono- and diglycerides and free fatty acids represent the component of the human food having the specifically highest energy content. About 40 percent of the whole calory content introduced by the average human food originates from the consumption of about daily 100 g of lipids. In a healthy condition, at most 5 percent of the consumed fats are eliminated by the faeces as undigested. The triglycerides are insoluble in water, the hydrolysis of which mainly to fatty acids and monoglycerides is catalyzed by the pancreas lipase at the upper part of the small intestine. The presence of the bile acids is needed for the optimum activity of lipase. Under the solubilizing effect of the bile acids, the lipids are dispersed to fine particles. The presence of the bile is needed not only to the enzymatic decomposition but also to the absorption of the water-insoluble products of the lipolysis. The natural bile contains cholic acid and deoxycholic acid as well as very little amounts of two additional cholic acid derivatives which are cholanic acid derivatives hydroxylated to a various extent. In the bile the bile acids, as bound to glycine or taurine, form glycocholic acid or taurocholic acid occuring in the form of water-soluble sodium salts. The functional parts of the bile which enter the intestine are represented by the bile acids, 90 percent of which are re-absorbed from the blood and recirculated. The bile acids appear in the urine only in the case when the liver function is damaged. The bile acids are not decomposed in the organism. They are toxic and exert a haemolytic effect when getting to the blood circulation.

The reasons for the malabsorption of the lipids may be the diminished synthesis and inhibited access of the bile acids to the intestines, the decrease in the active concentration of the conjugated bile acids or an enhanced loss of bile acids. The symptoms occurring as a consequence of the lipid malabsorption are distention, intestinal spasms, frequent abnormal discharge of faeces, diarrhoea, calory loss, weight loss as well as symptoms indicating a hypovitaminosis appearing as a consequence of the diminished absorption of fat-soluble vitamins.

In the case of lipid malabsorption, the natural bile has to be substituted. In the course of the therapeutical processes used at present, the bile is substituted by the salts of bile acids or by detergent-type compounds. Bile acid salts are e.g. in Suprachol dragée (dehydrocholic acid), Bilagit dragée e (sodium cholate), Bilival tablet (the complex of sodium cholate formed with lecithin).

As detergents e.g. Tween 60, Polysorbate 80, etc. are used which are mixtures of the stearates and oleates of polyalcohols.

The disadvantage of the use of detergents consists in that those should be employed in relatively high doses (about 6 g/day), as they form with the lipids only micelles instead of complexes of high stability, whereby a useful effect can only be achieved by higher quantities.

By using medicines containing bile acids, the bile production is increased. If bile acids are given for substituting the natural bile in cases when the bile cannot flow into the intestine (e.g. in the case of a cholecyst fistula), then the inhibited fat resorption can be improved by bile acids introduced orally, however, when the access of the bile acids to the intestine is hindered, the patient must not be given medicaments containing bile acids (e.g. in the case of icterus or a biliary attack). Similarly, it is not suitable to administer bile acids to patients suffering from hepatitis, as the damaged liver function would be loaded by the bile acids recirculating in the organism. In addition, the promotion of the fat digestion by administering bile acids is contraindicated by the close relation of the blood cholesterol level to the administration of bile acids.

Thus, a method of promoting the fat digestion and absorption is needed when the function of the natural bile is not completely normal; however, it is frequently disadvantageous when bile acids are used as bile-substituting agents.

The aim of the present invention is to provide a method for replacing the natural bile, by orally administering a completely different type of compound in comparison to the compounds used so far and which is not a compound secreted through the liver and discharged into the gall bladder.

Surprisingly, it was found that methylated cyclodextrins having an average substitution degree of 14 are useful for this purpose.

By decomposing starch with a specific starch-decomposing enzyme, the so-called cyclodextrin-transglycosilase enzyme, cyclic dextrins, i.e. the α-, β- and γ-cyclodextrins, respectively, containing six, seven or eight glucose moieties, respectively, can be prepared. It is characteristic of these cyclodextrins that they are soluble in water and form inclusion complexes with various apolar molecules (guest molecules) of adequate size. The water solibility of the inclusion complexes is low.

It has been shown by earlier studies that the water solubility of partially methylated derivatives of cyclodextrins is significantly higher as compared to that of the unsubstituted cyclodextrins. Simultaneously, the water solubility of the inclusion complexes of methylated cyclodextrins is much better than that of the inclusion complexes of cyclodextrins. Thus, injectable solutions of water-insoluble or nearly insoluble substance can be prepared by the means of complex formation with methylated cyclodextrins.

Among all of the methylated beta cyclodextrin derivatives having an average substitution degree of 14, heptakis(2,6-di-O-methyl)-β-cyclodextrin seems to be most suitable for the practical use, as the solubility of the higher or lower partially methylated cyclodextrins is less. The heptakis(2,6-di-O-methyl)-β-cyclodextrin (referred in the following as DIMEB) is a white powder having a very high water solubility and a particular property that on heating, it suddenly crystallizes out at a temperature (45° to 60° C.) depending on the concentration conditions, then on cooling it is re-dissolved. The DIMEB is prepared by the partial methylation of β-cyclodextrin. This reaction can be accomplished by using various known processes (disclosed e.g. in Hungarian patent specification No. 180 580 and Hungarian patent application No. 838/83). This substance is soluble in organic solvents, too. According to the animal experiments said substance is not absorbed after oral administvation and no toxic phenomena have been observed on mice after administering doses up to 3000 mg/kg of body-weight. After intravenous administration, DIMEB is completely eliminated through the kidneys within 6 hours.

According to Hungarian Patent 180,580 and the equivalent West German Laid-Open Application 3,118,218, the methylated-beta-cyclodextrin is not pure heptakis-(2,6-di-O-methyl)-beta-cyclodextrin, but a mixture of methylated-beta-cyclodextrins having slightly different degrees of methylation. The methylated-beta-cyclodextrin thus is characterized best by giving its average degree of methylation. The methylated-beta-cyclodextrin disclosed in each of said patent applications, the contents of which are expressly incorporated herein by reference, and employed according to the present method of treatment has an average substitution degree of 14.

All of the methylated-beta-cyclodextrins having an average substitution degree of 14 have only slightly different degrees of methylation, and are very similar to each other regarding both their physical, chemical and biological properties.

Surprisingly, it was found that the fat content of the food is disperged by forming an inclusion complex with DIMEB, whereby the fat content will be accessible to the decomposition by lipase and the digestion and absorption of fats will be promoted. Thus, DIMEB is suitable for replacing the natural bile. This bile-substituting role of DIMEB was proved in both in vitro and in vivo experiments.

Under in vitro conditions, the hydrolysis of triglycerides by lipase was studied and it was found that the activity of lipase was increased in DIMEB solutions.

Under in vivo conditions, the role of DIMEB was investigated on the digestion and absorption, respectively of fats in various experimental animals (rats, rabbits etc.). In the course of these investigations, after having prevented by a surgical operation that the experimental animals use their own bile, DIMEB was administered orally simultaneously with the trigylcerides. It was observed that the digestion and absorption of fats were normalized under effect of DIMEB.

Thus, the present invention relates to a method of treatment to replace the bile and to promote the digestion and absorption of fats, which contains a methylated-beta-cyclodextrin, having an average substitution degree of 14, preferably pure DIMEB for replacing the natural bile.

As the deficient fat digestion, which is the consequence of the insufficient bile function, results in microbial decomposition processes accompanied with painful intestinal spasms, the methylated-beta-cyclodextrins may suitably be formulated with disinfecting, spasmolytic active ingredients, as well as components improving the intestinal peristaltics and digesting enzymes.

The preparation of compositions suitable for carrying out the invention as well as the investigation of the bile-substituting effect of DIMEB under in vitro and in vivo experimental conditions are described in detail by the aid of the following non-limiting Examples.

EXAMPLES ILLUSTRATING THE PHARMACEUTICAL COMPOSITIONS OF THE INVENTION

Example 1

| | |
|---|---|
| Heptakis(2,6-di-O—methyl)-β-cyclodextrin | 250 mg |
| Talc | 50 mg |
| Polyvidone | 10 mg |
| Magnesium stearate | 4 mg |
| Lactose | 36 mg |
| | 350 mg |

The active ingredients are homogenized with the additives and granulated with the ethanolic solution of polyvidone. After drying, the granulate is pressed to tablets of 350 mg according to known methods of the tablet compression.

Example 2

| | |
|---|---|
| Heptakis(2,6-di-O—methyl)-β-cyclodextrin | 50 mg |
| Lactose | 25 mg |
| Talc | 19 mg |
| Magnesium stearate | 2 mg |
| Polyvidone | 4 mg |
| | 100 mg |

For preparing the tablets, the process of Example 1 is followed, except that the granulate is compressed to tablets weighing 100 mg.

Example 3

| | |
|---|---|
| Heptakis(2,6-di-O—methyl)-β-cyclodextrin | 200 mg |
| Papaverine hydrochloride | 20 mg |
| Sodium choleinate | 50 mg |
| Talc | 14 mg |
| Lactose | 10 mg |
| Magnesium stearate | 4 mg |
| Polyvidone | 2 mg |
| | 300 mg |

For preparing the dragée core, the process of Example 1 is followed. The coating is carried out in an overpressure equipment according to methods of the film coating known per se.

Example 4

| | |
|---|---|
| Heptakis(2,6-di-O—methyl)-β-cyclodextrin | 150 mg |
| Polyoxyethylene sorbitan monostearate (Tween 60) | 150 mg |
| Aerosil 972 | 12 mg |
| Magnesium stearate | 4 mg |
| Talc | 30 mg |
| Polyvidone | 4 mg |
| | 350 mg |

Tween 60 is homogenized with the aerosil in small portions, then after mixing in the active ingredients and the additives, the mixture is granulated with the ethanolic solution of polyvidone. After drying, the granulate is compressed to tablets.

Examples illustrating the activity of the methylated-beta-cyclodextrins having an average substitution degree of 14

Example 5

Increase of the lipase activity in dimethyl-β-cyclodextrin solutions

In an aqueous medium, lipase is capable to split triglycerides only at an extraordinarily low rate. Therefore, an organic solvent should be added to the system, by which the solubility of the triglycerides is increased, but the enzyme activity is diminished. Alternatively, some type of detergent, suitably bile has to be used. The effect of bile was compared to that of DIMEB at 37° C. in such a way that, the quantity of the formed free fatty acids in the samples taken from the reaction mixture at various intervals was titrated by using sodium hydroxide solution. The composition of the reaction mixture was as follows:

a total volume of 1.5 ml contained 4 μmoles of the substrate (triolein or olive oil), 10 mg of bovine serum albumin, 75 μmoles of sodium chloride, 50 μmoles of a phosphate buffer solution (pH 7.4) and 0.25 ml of an enzyme solution. A lipase of the Serva Company (in an 1 mg/10 ml solution) or a pancreas powder (0.5 g was suspended in 10 ml of distilled water and the slightly opalescent solution obtained after filtration was used) were employed as enzyme preparations.

The composition of the solutions to be tested were as follows:

0.5 ml of buffer+10 mg of serum albumin+3.54 mg of substrate+0.25 ml of enzyme solution plus (a) 0.25 ml of diluted bile+0.50 ml of distilled water; or (b) 50 mg of dimethyl-β-cyclodextrin dissolved in 0.75 ml of water; or (c) 0.75 ml of water.

It is obvious from Table 1 that dimethyl-β-cyclodextrin is capable to accelerate the action of lipase to a significant extent.

For the sake of simplicity, dimethyl-β-cyclodextrin is hereinafter abbreviated by the symbol "DIMEB".

TABLE I

In vitro enzymatic hydrolysis of triglycerides in the presence of bile or DIMEB

| Reaction time (hour) | 0.005 N NaOH consumed (ml) | | |
|---|---|---|---|
| | (a) (Bile) | (b) (DIMEB) | (c) (Control) |
| Bile I: swine bile 5-fold diluted; substrate: olive oil; enzyme: pancreas suspension | | | |
| 0.5 | 0.82 | 1.74 | 0.0 |
| 1 | 1.17 | 2.00 | 0.36 |
| 2 | 1.37 | 2.20 | 0.48 |
| 19 | 2.62 | 4.77 | 0.63 |
| Increase in the reaction rate | 4 times | 7.4 times | |
| Bile II: Chicken bile 10-fold diluted; substrate: glycerol trioleate; enzyme: lipase | | | |
| 1 | 0.20 | 0.34 | 0.0 |
| 2 | 0.32 | 0.80 | 0 |
| 3 | 0.48 | 1.16 | 0 |
| 21 | 0.58 | 1.86 | 0.1 |
| Increase in the reaction rate | 6 times | 18 times | |
| Bile III: Chicken bile 5-fold diluted substrate: glycerol triolate; enzyme: lipase | | | |
| 1 | 0.26 | 0.28 | 0 |
| 2 | 0.46 | 0.68 | 0 |

TABLE I-continued

In vitro enzymatic hydrolysis of triglycerides in the presence of bile or DIMEB

| Reaction time (hour) | 0.005 N NaOH consumed (ml) | | |
|---|---|---|---|
| | (a) (Bile) | (b) (DIMEB) | (c) (Control) |
| 4 | 0.74 | 1.20 | 0.14 |
| Increase in the reaction rate | 5 times | 8.5 times | |

Example 6

Enhancement of the lipid absorption in intact rats after oral administration of DIMEB The effect of DIMEB on the absorption of a vegetable oil was investigated in intact rats. The aim of this experiment was to elucidate whether the emulsification and intestinal absorption of the vegetable oil were stimulated by DIMEB in addition to the physiological bile functions. The experimental animals were simultaneously administered orally 2 ml of sunflower oil and 50 mg of DIMEB by using a gastric tube. Thereafter, the triglyceride and free fatty acid concentration of the blood plasma were examined at various intervals. (Tables II and III).

No significant difference was observed between the plasma triglyceride levels of the control and that of the treated groups within the first hour after treatment (Table II). In the 4th hour no significant deviation existed between the triglyceride concentrations of the control and that of the oil-treated group, a fact showing that the digestion was in progress; however, a significantly higher plasma triglyceride concentration was observed in the group of animals treated with the oil and DIMEB in comparison to both the control and to the group treated by the oil alone. The plasma triglyceride concentration was increased by more than 100 percent at the 4th hour by using DIMEB. At the 6th hour the plasma triglyceride level of the animals treated with the oil was also significantly increased as compared to the control, however, this value was still significantly lower than in the group treated with oil plus DIMEB. Similar trends were also observed concerning the free fatty acids (Table III).

The triglyceride concentration of the plasma was determined by using the method of E. Van Handel [Clin. Chem.. 7, 249 (1961)], whereas the concentration of the free fatty acids was measured according to W. G. Dumcombe [Biochem. J. 88, 7 (1963)].

TABLE II

Plasma triglyceride concentration in the plasma of normal rats as expressed in mg/100 ml (treatment with 2 ml of vegetable oil or with 2 ml of vegetable oil together with 50 mg of DIMEB, respectively)

| | Control | Oil | Oil + DIMEB |
|---|---|---|---|
| Hour 0 | 49 ± 12 | | |
| Hour 1 | | 43 ± 8 | 44 ± 6 |
| Hour 2.5 | | 72 ± 18 | 61 ± 18 |
| Hour 4 | | 58 ± 11 | 121 ± 7 |
| Hour 6 | | 88 ± 5 | 122 ± 15 |

TABLE III

Free fatty acid concentration in the plasma of normal rats as expressed in mg/100 ml (treatment with 2 ml of vegetable oil or with 2 ml of vegetable oil together with 50 ml of DIMEB, respectively)

|          | Control  | Oil        | Oil + DIMEB |
|----------|----------|------------|-------------|
| Hour 0   | 97 ± 36  |            |             |
| Hour 1   |          | 240 ± 70   | 326 ± 15    |
| Hour 2.5 |          | 421 ± 146  | 494 ± 183   |
| Hour 4   |          | 318 ± 93   | 641 ± 126   |
| Hour 6   |          | 412 ± 88   | 347 ± 65    |

Thus, it has been proved by the experimental results reported above that the absorption of lipids introduced in the form of triglycerides to the intestines was effectively enhanced by using DIMEB in healthy, intact animals.

Example 7

Substitution of the bile in rabbits

The experimental animals were prevented in using their own bile for digestion of lipids by ligating their bile duct. Triglyceride concentration of the blood plasma was investigated after oral administration of lipids under normal pancreas secretion.

The experimental rabbits (Orychtolagus cuniculus) were kept at a standard food fo 10 days before the experiment. The organic material composition of the animal food was as follows:

| Crude protein         | 16.0% |
| Soluble carbohydrates | 42.7% |
| Crude fibres          | 12.6% |
| Crude fat             | 7.3%  |
| Vitamin mixture       | 1.0%  |

The energy content of 100 g of the food amounted to 1360 Joules. The animals were starved for 12 to 24 hours before the surgical operations but received water ad libitum. Within the same experimental series, rabbits of the same sex with a body weight of 2500 to 3000 g were used and the surgical operations were concurrently carried out. Pseudo-operated animals were used as controls. The operated experimental animals were used for the investigations after 48 hours. The test substances were orally administered to the animals through a gastric tube. The blood samples were taken from the auricular marginal vene.

In the first series of experiments, the first group of animals were given 3 ml of sunflower oil, the second group of animals were given 3 ml of sunflower oil and 200 mg of DIMEB dissolved in 3 ml of water. The control (speudo-operated) animals received 6 ml of water. According to the data of Table IV the digestion of the lipids is very slow in the absence of bile acids and in the presence of lipase, considering that the plasma triglyceride concentration was not significantly increased within the experimental period lasting 6 hours. The group given DIMEB simultaneously with the administration of the vegetable oil showed an obvious and significant increase in the triglyceride level starting from the first hour. In the 6th hour, a nearly three-fold triglyceride concentration was measured in the plasma of the group treated with the vegetable oil together with DIMEB as compared with the plasma level measured in the group treated with oil alone.

It is known that the digestion of the fats is a slower process than that of the oils. Thus, in the second series of experiments, the changes of the plasma triglyceride concentration of bile duct-ligated rabbits were followed after the oral administration of 5 ml of swine fat and 5 ml of swine fat together with 300 mg of DIMEB, respectively. The control group was given 5 ml of water (Table V). The quantity of the triglycerides was increased by about 100 percent as compared to the other two groups within one hour following the treatment. This tendency permanently remained during the experimental period lasting 6 hours. The values measured at any time point were significantly higher than those of the two other groups.

Thus, it has unambiguously been proved by this two series of experiments that the absorption of triglycerides could significantly be promoted by DIMEB in an acute experimental bile acid deficiency, i.e. the natural bile could be substituted by DIMEB. The dispersing of the lipids, the digesting function of lipase and the absorption of the liberated fatty acids are promoted by DIMEB.

TABLE IV

The effect of treatment on the plasma triglyceride concentration of rabbits after bile duct ligature as expressed in mg/100 ml (treatment with 3 ml of sunflower oil or with 3 ml of sunflower oil together with 200 mg of DIMEB, respectively; control: 6 ml of water)
Absolute control: 51.0 ± 13.82 mg/100 ml
Operated control at 0 hour: 49.03 ± 16.57 mg/100 ml

|          | Control  | Oil     | Oil + DIMEB |
|----------|----------|---------|-------------|
| Hour 0   | 36 ± 7   | 46 ± 5  | 52 ± 19     |
| Hour 1   | 34 ± 5   | 57 ± 10 | 96 ± 32     |
| Hour 2.5 | 30 ± 5   | 47 ± 10 | 87 ± 30     |
| Hour 4   | 46 ± 10  | 40 ± 6  | 61 ± 14     |
| Hour 6   | 70 ± 6   | 45 ± 10 | 125 ± 3     |

TABLE V

The effect of treatment on the plasma triglyceride concentration of rabbits after bile duct ligature as expressed in mg/100 ml (treatment with 5 ml of swine fat or with 5 ml of swine fat together with 300 mg of DIMEB; control: 6 ml of water)

|          | Control  | Oil     | Oil + DIMEB |
|----------|----------|---------|-------------|
| Hour 0   | 49 ± 14  | 46 ± 5  | 58 ± 19     |
| Hour 1   | 34 ± 5   | 57 ± 10 | 104 ± 30    |
| Hour 2.5 | 30 ± 5   | 47 ± 10 | 92 ± 26     |
| Hour 4   | 46 ± 10  | 40 ± 6  | 83 ± 25     |
| Hour 6   | 70 ± 6   | 45 ± 10 | 125 ± 3     |

Example 8

Substitution of the bile in rats

In the first series of experiments, the total lipid concentration of the plasma was investigated in bile-deficient rats.

The experimental rats (Etymis rattus var. albino) were kept on a standard food for 10 days before the experiment. The composition of this animal food was as follows:

| Crude protein         | 19.6% |
| Crude fibres          | 5.6%  |
| Soluble carbohydrates | 49.2% |
| Fat                   | 4.6%  |
| Vitamin mixture       | 1.0%  |

The energy content of 100 g of the food amounted to 1382 Joules.

The bile duct was ligated under ether anaesthesia.

In the 48th hour following the operation, 1.5 ml of swine fat or 1.5 ml of swine fat together with 75 mg of DIMEB were orally administered. After 4.5 hours, the animals were decapitated and the total lipid concentration of the plasma was determined according to the method of de La Huerga et al. [Amer. J. Clin. Pathol. 23, 1163 (1953)]

According to the data of Table VI, the total lipid concentration did not significantly change after the ligature. A significant increase in the total lipid concentration was observed in the bile duct-ligated animals treated with only fat as compared to either the former group as well as to the control group. A highly important and very significant increase in the total lipid concentration was observed in the animal group treated with fat together with DIMEB as compared to all the three animal groups. The total lipid fraction in the blood plasma was increased to the 2.5-fold in the animals treated with fat and to the 5-fold in those treated with fat together with DIMEB.

In an other series of experiments, the total lipid content of the faeces discharged by bile-deficient rats was studied.

The oral treatment was started with the daily administration of 1 ml of swine fat or 1 ml of swine fat together with 150 mg of DIMEB, respectively, in the 72nd hour following the ligature. The treatment was continued for 5 days. The faeces was collected in the first 4 days of the treatment. In the 4th hour following the treatment on the 5th day, the experimental animals were decapitated and their samples were worked up. The changes in the lipid quantities discharged with the faeces during 4 days are shown in Table VII. The concentration of the discharged lipid was significantly higher in the faeces of the bile duct-ligated animals fed in a similar way than in that of the intact control rats kept on a standard food. An extraordinarily high amount of lipids were eliminated with the faeces of the animals fed with fat. The lipid discharge, however, was dramatically reduced by the administration of daily 150 mg of DIMEB. Nearly 100 percent of the introduced fat was absorbed under the effect of DIMEB.

The development of the total lipid, triglyceride concentration of the plasma and the triglyceride concentration of the liver, shown in Table VIII was in complete agreement with these results. The concentration of the total lipids in the plasma was significantly higher in the animal group treated with fat or with fat together with DIMEB, respectively, than the corresponding values observed in the bile duct-ligated or control group. It is important, however, that the total lipid concentration in the plasma of the animals treated with fat together with DIMEB proved to be significantly higher than that of the animals treated with fat only.

The triglyceride concentration of the plasma showed a similar tendency. A significant deviation was observed between the groups treated with fat or with fat together with DIMEB, respectively. The triglyceride concentration of the liver was significantly reduced in the bile duct-ligated group which did not receive any other treatment. The triglyceride concentration was restored in this group to the control value by the treatment with fat. A significant increase in the triglyceride concentration was induced by the treatment with fat together with DIMEB in comparison to the former group.

In order to prove that the increase in the blood lipid level arose from the enhancement of the fat absorption but not from the mobilization of the lipid content of the organs (liver, fat tissue), rats kept on a normal food were orally treated by administering DIMEB in a daily dose of 150 mg/kg or 300 mg/kg, respectively, for 31 days. According to the resuts summarized in Table IX, neither the plasma, nor the liver triglyceride content were influenced by DIMEB.

TABLE VI

The effect of the treatment on the total lipid concentration of the blood plasma of rats after bile duct-ligation as expressed in mg/100 ml (treatment with 1.5 ml of fat or 1.5 ml of fat together with 75 mg of DIMEB, respectively)

| Control: | |
| --- | --- |
| before the ligation | 207.1 ± 43.3 |
| after the ligation | 266.6 ± 39.5 |
| Treatment: | |
| with fat | 657.7 ± 262.6 |
| with fat + DIMEB | 1266.6 ± 86.5 |

TABLE VII

The fat discharge of bile acid-deficient rats as expressed in g/100 g (treatment with daily 1 ml of fat or 1 ml of fat together with 150 mg of DIMEB, respectively, for 5 days)

| Control: | |
| --- | --- |
| before the ligation | 0.44 ± 0.23 |
| after the ligation | 4.08 ± 1.96 |
| Treatment: | |
| with fat | 27.55 ± 4.72 |
| with fat + DIMEB | 6.16 ± 2.37 |

TABLE VIII

The plasma total lipid, plasma triglyceride and liver triglyceride concentration, respectively, of bile acid-deficient rats after a treatment lasting 5 days as expressed in mg/100 ml

| | Total lipids | Plasma triglycerides | Liver triglycerides |
| --- | --- | --- | --- |
| Control: | | | |
| before ligation | 281. ± 54.5 | 35.4 ± 4.8 | 7.3 ± 1.6 |
| after ligation | 319.9 ± 32.3 | 28.1 ± 4.3 | 4.2 ± 0.3 |
| Treatment: | | | |
| with fat | 528.3 ± 111.2 | 40.1 ± 11.5 | 6.4 ± 1.9 |
| with fat + DIMEB | 688.7 ± 95.8 | 71.9 ± 19.1 | 9.1 ± 2.2 |

TABLE IX

Effect of an oral treatment lasting 31 days with a daily dose of 150 mg/kg or 300 mg/kg, respectively, of DIMEB on normal rats as expressed in mg/100 ml

| | Plasma triglycerides | Liver triglycerides |
| --- | --- | --- |
| Control | 52.5 ± 7.4 | 4.5 ± 0.9 |
| 150 mg/kg of DIMEB | 48.3 + 4.5 | 3.6 ± 1.0 |
| 300 mg/kg of DIMEB | 45.9 ± 3.1 | 3.8 ± 1.4 |

Example 9

Investigation of the absorption of $^3H$ stearic acid with the simultaneous oral administration of DIMEB in intact rats The effect of DIMEB on the absorption of $^3H$-stearic acid was studied in intact rats. The aim of this experiment was to make clear if the absorption of stearic acid was stimulated by DIMEB under the conditions of physiological bile functions. The animals were starved overnight before and during the experiment but received water ad libitum. One group of the experimental animals (CFY female rats with an average body weight of 180 g; 3 animals) received 13 mg of $^3$H-stearic acid (specific radioactivity: 147.22 kBq/mg), whereas the other group (3 animals) was given 11.3 mg of $^3$H-stearic acid and 50 mg of DIMEB in 2 ml of distilled water. The substances were suspended in the distilled water ultrasonically. Thereafter, the radioactivity level of the blood was measured at various time intervals by using the liquid scintillation method (Table X).

No difference was observed between the blood levels of these two groups. The radioactivity level of the blood was 1.8 to 1.9 percent of the administered radioactivity at one hour following treatment and then it slowly increased. The radioactivity of the blood was 2.7 percent of the administered activity at the 24th hour. Thus, DIMEB did not show any absorption-enhancing effect under the conditions of physiological bile functions.

TABLE X

The radioactivity measured in 10 ml of blood of intact rats as expressed in percentage of the total radioactivity administered (treatment with 13 mg of $^3$H-stearic acid or with 11.3 mg of $^3$H-stearic acid together with 50 mg of DIMEB in 2 ml of distilled water, respectively)

| Time | $^3$H-stearic acid | | | | $^3$H-stearic acid + DIMEB | | | |
|---|---|---|---|---|---|---|---|---|
| (hours) | 1 | 2 | 3 | $\bar{x}$ | 4 | 5 | 6 | $\bar{x}$ |
| 1 | 1.92 | 1.97 | 1.47 | 1.79 | 1.71 | 1.74 | 2.23 | 1.89 |
| 2 | 1.95 | 2.10 | 1.93 | 1.99 | 1.84 | 1.88 | 2.00 | 1.91 |
| 3 | 2.15 | 1.97 | 2.03 | 2.05 | 2.03 | 1.75 | 2.13 | 1.97 |
| 4 | 2.12 | 1.98 | 2.11 | 2.07 | 2.12 | 1.71 | 1.99 | 1.94 |
| 5 | 2.11 | 1.89 | 2.12 | 2.04 | 2.10 | 1.76 | 2.00 | 1.95 |
| 6 | 2.08 | 1.87 | 2.15 | 2.03 | 2.16 | 1.75 | 2.04 | 1.98 |
| 8 | 2.35 | 1.93 | 2.23 | 2.17 | 2.16 | 1.84 | 1.94 | 1.98 |
| 10 | 2.59 | 2.39 | 2.50 | 2.49 | 2.20 | 2.02 | 2.21 | 2.14 |
| 24 | 2.97 | 2.63 | 2.43 | 2.68 | 2.84 | 2.94 | 2.39 | 2.72 |

Example 10

Investigation of the absorption of $^3$H-stearic acid with the simultaneous oral administration of DIMEB in bile-deficient rats The substitution of the bile by DIMEB in bile-deficiency was studied in rats after ligating the bile duct.

After being starved for 24 hours, the animals were subjected to the bile duct-ligation under nembutal anaesthesia. The absorption was investigated in the 48th hour after starving the animals overnight. The animals were also starved in the course of the examination; but received water ad libitum. One group (3 animals) received 12.8 mg of $^3$H-stearic acid (specific radioactivity: 171.12 kBq/mg), whereas the other group (3 animals) was administered 14.7 mg of $^3$H-stearic acid and 50 mg of DIMEB in 2 ml of distilled water. The substances were suspended in the distilled water ultrasonically. Thereafter, the radioactivity level of the blood was measured at various intervals, by using the liquid scintillation method (Table XI).

A significant difference was found between the the blood levels of the two groups. The radioactivity level of a 10 ml blood sample was 1.97 percent of the administered radioactivity at one hour following treatment, whereas the radioactivity of the blood was 0.73 percent of the administered activity in the group treated with $^3$H-stearic acid. In the 24th hour, the blood level of the animals treated with $^3$H-stearic acid together with DIMEB was 1.4-times as high as the blood level of the animals treated with stearic acid only. Thus, the absorption of the fatty acid was promoted by DIMEB in the experimentally bile-deficient animals.

TABLE XI

The radioactivity measured in 10 ml of blood of bile-deficient rats as expressed in percentage of the total radioactivity administered (treatment with 12.8 mg of $^3$H-stearic acid or with 14.7 mg of $^3$H-stearic acid together with 50 mg of DIMEB in 2 ml distilled water, respectively)

| Time | $^3$H-stearic acid | | | | $^3$H-stearic acid + DIMEB | | | |
|---|---|---|---|---|---|---|---|---|
| (hours) | 1 | 2 | 3 | $\bar{x}$ | 4 | 5 | 6 | $\bar{x}$ |
| 1 | 0.59 | 0.82 | 0.78 | 0.73 | 0.86 | 3.45 | 1.61 | 1.97 |
| 2 | 0.68 | 1.06 | 1.06 | 0.93 | 1.05 | 3.25 | 2.56 | 2.29 |
| 3 | 0.77 | 1.19 | 1.16 | 1.04 | 1.14 | 3.22 | 2.39 | 2.25 |
| 4 | 0.84 | 1.32 | 1.30 | 1.15 | 1.19 | 3.06 | 2.28 | 2.18 |
| 5 | 0.92 | — | 1.50 | 1.21 | 1.24 | 3.08 | 2.27 | 2.20 |
| 6 | 0.93 | 1.50 | 1.51 | 1.31 | 1.25 | 2.91 | 2.56 | 2.24 |
| 7 | 0.96 | 1.68 | 1.64 | 1.43 | 1.33 | 3.03 | 2.67 | 2.34 |
| 8 | 1.10 | 1.65 | 1.67 | 1.47 | 1.37 | 3.13 | 2.58 | 2.36 |
| 10 | 1.10 | 1.84 | 1.57 | 1.50 | 1.29 | 3.26 | 2.67 | 2.41 |
| 24 | 2.44 | 2.60 | 2.09 | 2.38 | 1.60 | 4.56 | 4.00 | 3.39 |

Example 11

Investigation of the absorption of $^3$H-stearic acid with the simultaneous oral administration of DIMEB in bile-dificient rats The substitution by DIMEB of the bile in bile-deficiency was studied in rats after ligating the bile duct.

After being starved for 24 hours, the animals (CFY female rats with an average body weight of 150 g) were subjected to a bile duct-ligation under nembutal anaesthesia. The absorption was investigated in the 48th hour after starving the animals overnight. The animals were starved in the course of the examination, too, but received water ad libitum. One group (consisting of 4 animals) received 22.2 mg of $^3$H-stearic acid (specific radioactivity: 92.5 kBq/mg), whereas the other group (consisting of 4 animals) was administered 23.5 mg of $^3$H-stearic acid and 60 mg of DIMEB in 2 ml of distilled water. The substances were suspended ultrasonically in the distilled water. Thereafter, the radioactivity level of the blood was measured at various intervals by using the liquid scintillation method (Table XII).

A significant difference was found between the blood levels of the two groups. The radioactivity of the blood level of animals treated with $^3$H-stearic acid together with DIMEB was 4.4-times as high, then this difference slowly decreased and in the 24th hour, the blood level of the animals treated with $^3$H-stearic acid together with DIMEB was only 2-times as high as that of the animals treated with stearic acid alone.

Thus, the absorption of the fatty acids was promoted by DIMEB in the experimentally bile-deficient animals.

TABLE XII

The radioactivity measured in 10 ml of blood of bile-deficient rats as expressed in percentage of the total radioactivity administered (treatment with 22.2 mg of $^3$H-stearic acid or with 23.5 mg of $^3$H-stearic acid together with 60 mg of DIMEB, respectively)

| Time | $^3$H-stearic acid | | | | | $^3$H-stearic acid + DIMEB | | | | |
|---|---|---|---|---|---|---|---|---|---|---|
| (hours) | 1 | 2 | 3 | 4 | $\bar{x}$ | 5 | 6 | 7 | 8 | $\bar{x}$ |
| 1 | 0.26 | 0.36 | 0.22 | 0.24 | 0.27 | 1.18 | 1.41 | 1.66 | 0.50 | 1.19 |

TABLE XII-continued

The radioactivity measured in 10 ml of blood of bile-deficient rats as expressed in percentage of the total radioactivity administered (treatment with 22.2 mg of $^3$H-stearic acid or with 23.5 mg of $^3$H-stearic acid together with 60 mg of DIMEB, respectively)

| Time (hours) | $^3$H-stearic acid | | | | | $^3$H-stearic acid + DIMEB | | | | |
|---|---|---|---|---|---|---|---|---|---|---|
| | 1 | 2 | 3 | 4 | $\bar{x}$ | 5 | 6 | 7 | 8 | $\bar{x}$ |
| 2 | 0.43 | 0.57 | 0.29 | 0.35 | 0.41 | 1.46 | 1.52 | 1.52 | 0.64 | 1.28 |
| 3 | 0.53 | 0.75 | 0.37 | 0.33 | 0.49 | 1.29 | 1.63 | 1.37 | 0.61 | 1.22 |
| 4 | 0.62 | 0.76 | 0.43 | 0.38 | 0.55 | 1.42 | 1.67 | 1.56 | 0.60 | 1.31 |
| 5 | 0.57 | 0.85 | 0.50 | 0.39 | 0.56 | 1.39 | 1.73 | 1.54 | 0.69 | 1.34 |
| 6 | 0.59 | 0.85 | 0.55 | 0.40 | 0.60 | 1.41 | 1.92 | 1.76 | 0.73 | 1.45 |
| 8 | 0.57 | 0.96 | 0.83 | 0.43 | 0.70 | 1.43 | 1.90 | 1.85 | 0.72 | 1.47 |
| 10 | 0.71 | 0.91 | 0.83 | 0.47 | 0.73 | 1.57 | 1.56 | 1.45 | 0.89 | 1.37 |
| 24 | 0.74 | 0.82 | 0.86 | 1.03 | 0.86 | 1.50 | 1.94 | 1.59 | 1.95 | 1.74 |

What is claimed is:

1. A method of treating an animal subject deficient in the ability to secrete bile to facilitate lipid digestion and absorption, which comprises the step of orally administering to an animal subject in need of said treatment, a pharmaceutically effective amount of a methylated-beta-cyclodextrin having an average substitution degree of 14 together with an ingestible lipid.

2. The method of treating an animal subject defined in claim 1 wherein the methylated-beta-cyclodextrin having an average substitution degree of 14 is heptakis(2,6-di-O-methyl)-beta-cyclodextrin.

3. The method of treating an animal subject defined in claim 1 wherein the animal subject is a mammalian subject.

* * * * *